US010555552B2

(12) United States Patent
Batista et al.

(10) Patent No.: US 10,555,552 B2
(45) Date of Patent: Feb. 11, 2020

(54) AEROSOL GENERATING DEVICE WITH PIERCING ASSEMBLY

(71) Applicant: Altria Client Services LLC, Richmond, VA (US)

(72) Inventors: Rui Nuno Batista, Morges (CH); Laurent Manca, Sullens (CH)

(73) Assignee: Altria Client Servies LLC, Richmond, VA (US)

(*) Notice: Subject to any disclaimer, the term of this patent is extended or adjusted under 35 U.S.C. 154(b) by 207 days.

(21) Appl. No.: 15/607,977

(22) Filed: May 30, 2017

(65) Prior Publication Data

US 2017/0340003 A1 Nov. 30, 2017

Related U.S. Application Data

(63) Continuation of application No. PCT/EP2017/062720, filed on May 25, 2017.

(30) Foreign Application Priority Data

May 31, 2016 (EP) .................................... 16172186

(51) Int. Cl.
*A24F 47/00* (2006.01)
*A24B 15/167* (2020.01)
(Continued)

(52) U.S. Cl.
CPC .......... *A24B 15/167* (2016.11); *A24F 47/008* (2013.01); *A61L 9/014* (2013.01); *A61L 9/037* (2013.01); *A24F 47/00* (2013.01)

(58) Field of Classification Search
CPC ....... A24F 47/008; A24F 47/00; A61M 15/06; A61M 15/0036; A61M 15/0041;
(Continued)

(56) References Cited

U.S. PATENT DOCUMENTS

2010/0006113 A1 1/2010 Urtsev et al.

FOREIGN PATENT DOCUMENTS

| WO | WO-2009/132793 A1 | 11/2009 |
| WO | WO-2014/201432 A1 | 12/2014 |
| WO | WO-2015/197627 A1 | 12/2015 |

OTHER PUBLICATIONS

Written Opinion dated Aug. 16, 2017 for PCT/EP2017/062720.
(Continued)

*Primary Examiner* — Tan-Uyen T Ho
*Assistant Examiner* — Margaret M Luarca
(74) *Attorney, Agent, or Firm* — Harness, Dickey & Pierce, P.L.C.

(57) ABSTRACT

An electrically heated aerosol-generating device includes a main housing having a cavity, a closure body engageable with the main housing to enclose a cartridge in the cavity, and a heater assembly. The heater assembly includes an elongate piercing assembly configured to extend into the open-ended passage of the cartridge and one or more electric heaters. The piercing assembly has a first hollow shaft portion connected to the main housing and a second hollow shaft portion connected to the closure body. The first and second hollow shaft portions have first and second piercing surfaces configured to breakthrough first and second frangible seals when the cartridge is enclosed in the cavity.

10 Claims, 7 Drawing Sheets

(51) Int. Cl.
*A61L 9/03* (2006.01)
*A61L 9/014* (2006.01)

(58) Field of Classification Search
CPC ........ A61M 15/00345; A61M 15/0038; A61M 16/104; A61M 5/3129; A61M 11/007
See application file for complete search history.

(56) References Cited

OTHER PUBLICATIONS

International Preliminary Report on Patentability for corresponding International Application No. PCT/EP2017/062720 dated Dec. 13, 2018.
Extended European Search Report Application No. 16172186.5-1662 dated Dec. 8, 2016.

AEROSOL GENERATING DEVICE WITH PIERCING ASSEMBLY

CROSS-REFERENCE TO RELATED APPLICATIONS

This application is a continuation of, and claims priority to, international application No. PCT/EP2017/062720, filed on May 25, 2017, and further claims priority under 35 U.S.C. § 119 to European Patent Application No. 16172186.5, filed May 31, 2016, the entire contents of each of which are incorporated herein by reference.

BACKGROUND

Field

Example embodiments relate to an aerosol-generating device for use with a consumable cartridge. At least one example embodiment relates to an electrically heated aerosol-generating device for use with a consumable cartridge having an internal passage and containing an aerosol-forming substrate. At least one example embodiment relates to consumable cartridges for use with aerosol-generating devices, to electrically heated aerosol-generating systems comprising an electrically heated aerosol-generating device and a consumable cartridge, and to kits for an electrically heated aerosol-generating system comprising an electrically heated aerosol-generating device and a plurality of consumable cartridges.

Electrically heated smoking systems may be handheld and may operate by heating an aerosol-forming substrate in an aerosol-generating article, or cartridge. WO2009/132793 describes an electrically heated smoking system comprising a shell and a replaceable mouthpiece, the entire content of which is incorporated herein by reference thereto.

SUMMARY

At least one example embodiment relates to an electrically heated aerosol-generating device for use with a consumable cartridge comprising a storage portion containing an aerosol-forming substrate. The storage portion has a fluid permeable internal surface surrounding an open ended passage extending through the cartridge. The device comprises a main housing having a cavity for receiving a cartridge, a closure body engageable with the main housing to enclose the cartridge in the cavity, and a heater assembly for heating the cartridge. The heater assembly includes an elongate piercing assembly configured to extend into the open-ended passage of the cartridge and defining an internal airflow passage forming part of an airflow pathway through the device. The elongate piercing assembly includes a first hollow shaft portion connected to the main housing. The first hollow shaft portion has a first piercing surface at a distal end thereof. The first piercing surface is configured to break through a first frangible seal across a first end of the open ended passage when the cartridge is inserted into the cavity. The elongate piercing assembly also includes a second hollow shaft portion connected to the closure body. The second hollow shaft portion has a second piercing surface at a distal end thereof. The second piercing surface is configured to break through a second frangible seal across a second end of the open ended passage when the closure body is engaged with the main housing. The first and second hollow shaft portions extend along a same longitudinal axis when the closure body is engaged with the main housing. The first and second hollow shaft portions are sized to meet at a junction such that the elongate piercing assembly extends along an entire length of the cavity when the closure body is engaged with the main housing. The heater assembly also includes at least one electric heater fixed to the elongate piercing assembly. The at least one electric heater has at least one heating element configured to heat the aerosol forming substrate when the cartridge is enclosed in the cavity.

BRIEF DESCRIPTION OF THE DRAWINGS

The invention will be further described, by way of example only, with reference to the accompanying drawings.

DETAILED DESCRIPTION

Figure 1:
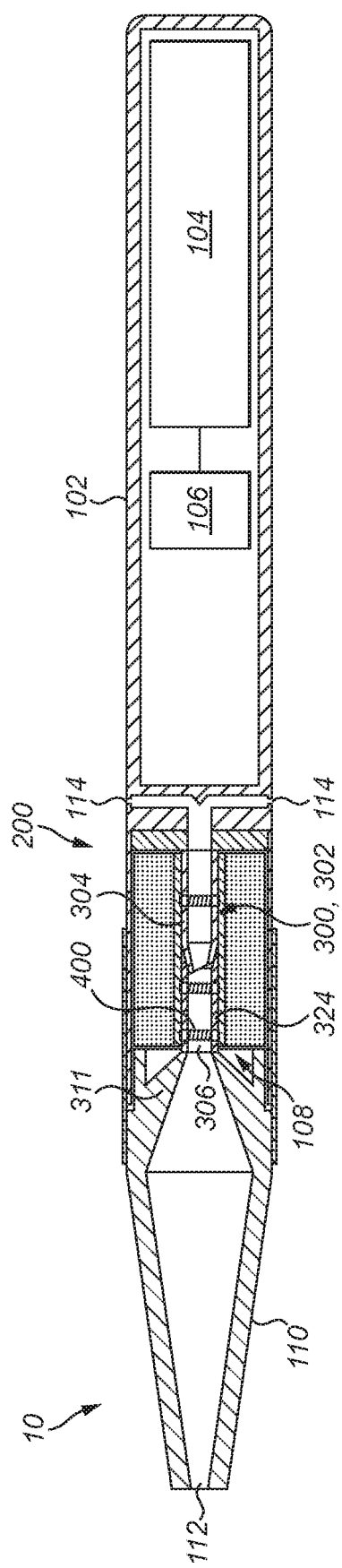
FIG. 1 illustrates a longitudinal cross-section of an aerosol-generating system according to a first embodiment.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

Further, one or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium", may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

According to at least one example embodiment, there is provided an electrically heated aerosol-generating device for use with a consumable cartridge comprising a storage portion containing an aerosol-forming substrate, the storage portion having a fluid permeable internal surface surrounding an open ended passage extending through the cartridge. The device comprises a main housing having a cavity for receiving a consumable cartridge; a closure body engageable with the main housing to enclose the cartridge in the cavity; and a heater assembly for heating the cartridge. The heater assembly comprises: an elongate piercing assembly arranged to extend into the open-ended passage of the cartridge and defining an internal airflow passage forming part of an airflow pathway through the device; and one or more electric heaters fixed to the elongate piercing assembly. The one or more electric heaters each have at least one heating element for heating the aerosol forming substrate when the cartridge is enclosed in the cavity. The elongate piercing assembly comprises a first hollow shaft portion connected to the main housing and has a first piercing surface at its distal end for breaking through a first frangible seal across a first end of the open ended passage when the cartridge is inserted into the cavity. The elongate piercing assembly also comprises a second hollow shaft portion connected to the closure body and has a second piercing surface at its distal end for breaking through a second frangible seal across a second end of the open ended passage when the closure body is engaged with the main housing. The first and second hollow shaft portions are arranged to extend along the same longitudinal axis when the closure body is engaged with the main housing. The first and second hollow shaft portions are sized to meet at a junction such that the elongate piercing assembly extends along the entire length of the cavity when the closure body is engaged with the main housing.

In at least one example embodiment, having a two-part piercing assembly may allow the seals at either ends of a cartridge to be more easily broken. By breaking the seals inwardly, the seals may be substantially prevented from moving away from the hollow shaft portions and the stresses exerted by the first and second piercing surfaces on the seals are higher, causing the seals to break more easily. Additionally, by connecting one of the hollow shaft portions to the closure body, it may be possible to substantially prevent the seal at the downstream end of the cartridge from being broken until the closure body is placed over the main housing. This may reduce the risk of liquid leakage during insertion of the cartridge. Further, by providing the electric heaters as part of the device, cartridges for use with the device may be simplified, less expensive and more robust than cartridges which include an electric heater. Accordingly, reducing the cost of cartridges, even if it requires a more expensive device, can lead to significant cost savings for both manufacturers and consumers.

The heater assembly comprises an elongate piercing assembly to which one or more electric heaters is fixed. Thus, the elongate piercing assembly doubles as a mount for the one or more electric heaters and as a piercing member. This may allow the elongate piercing assembly to pierce the seal at the end of a cartridge conveniently and easily during insertion of the cartridge into the device. To facilitate piercing of the seal, the distal ends of the first and second hollow shaft portions at which the first and second piercing surfaces are located have a cross-sectional area that is smaller than the cross-sectional area of the region of the hollow shaft member immediately proximal of the piercing surface. In at least one example embodiment, the cross-sectional areas of the first and second hollow shaft portions narrow towards a tapered tip at their respective distal ends. The cross-sectional areas of the first and second hollow shaft portions may narrow towards a point at their respective distal ends.

The elongate piercing assembly has an internal airflow passage forming part of an airflow pathway through the device. With this arrangement, the elongate piercing assembly may provide a support for the electric heaters as well as providing an airflow channel. This may allow for a device which is compact and may facilitate cost-effective high volume manufacturing. Having an airflow passage within the first and second hollow shaft portions may help to substantially minimise and/or reduce heat loss from the device and may allow the housing of the device to be easily maintained at a temperature which is comfortable to hold. Furthermore, vaporised aerosol-forming substrate in the air flow through the hollow shaft portions can begin to cool within the airflow passage to form an aerosol, allowing the overall length of the device to be reduced.

The frangible seals form barriers across the ends of the cartridge prior to insertion into the cavity of the device. The frangible seals may be made from any suitable material or materials, for example from a film, such as a metal film. In at least one example embodiment, the frangible seal may be formed of an aluminium film.

In at least one example embodiment, the first and second hollow shaft portions are arranged to extend along the same longitudinal axis when the closure body is engaged with the main housing.

The first and second hollow shaft portions are also sized to meet at a junction such that the elongate piercing assembly extends along the entire length of the cavity when the closure body is engaged with the main housing.

The distal ends of the first and second hollow shaft portions are co-operatively shaped such that a seal is formed around the junction. With this arrangement, air flow may be substantially confined to the internal airflow passage through the elongate piercing assembly, rather than passing into the storage portion of the cartridge, thereby facilitating the delivery of a consistent aerosol.

The distal ends of the first and second hollow shaft portions may have any suitable, co-operative piercing shape. In at least one example embodiment, the distal end of one of the first and second hollow shaft portions has an inwardly tapering outer surface and the distal end end of the other one of the first and second hollow shaft portions has an outwardly tapering inner surface, the inner and outer surfaces being shaped such that the inwardly tapering outer surface fits within the outwardly tapering inner surface to form the seal when the closure body is engaged with the main housing. This may allow the first and second hollow shaft portions to be mated easily. In at least one example embodiment, the distal end of the first hollow shaft portion may have an inwardly tapering outer surface and the distal end end of the second hollow shaft portion may have an outwardly tapering inner surface. The inner and outer surfaces re shaped such that the inwardly tapering Outer surface fits within the outwardly tapering inner surface to form the seal when the closure body is engaged with the main housing.

The closure body may function simply as a lid for closing the cavity. In at least one example embodiment, the closure body forms a mouthpiece portion by which air can be drawn through the airflow pathway of the aerosol generating device. The mouthpiece portion may have an outlet through which aerosol generated by the device can be drawn. As used herein, the term "mouthpiece portion" means a portion of the device that is configured to be drawn upon and through when the aerosol exits the device.

The first and second hollow shaft portions are electrically conductive. In at least one example embodiment, the first and second hollow shaft portions may be arranged to connect the one or more electric heaters to an electrical power supply. In at least one example embodiment, the first and second hollow shaft portions may be formed from an electrically conductive material, such as metal. In at least one example embodiment, the first and second hollow shaft portions may be formed from an electrically insulative substrate, such as a polymer substrate, and may further comprise one or more electrical conductors attached to the substrate for connecting the electric heaters to an electrical power source. In at least one example embodiment, the first and second hollow shaft portions may comprise an electrically insulative substrate on which electrical conductors are applied for example by deposition, printing, or by laminating with the substrate as a laminated foil. The laminate foil may then be shaped or folded to form the first and second hollow shaft portions.

The heater assembly may comprise a single electric heater comprising at least one heating element for heating the aerosol-forming substrate of a cartridge received in the cavity. In at least one example embodiment, the heater assembly comprises a plurality of electric heaters which are fixed to and spaced along the length of the elongate piercing assembly.

In at least one example embodiment, this arrangement may allow for more even heating of the aerosol-forming substrate in the cartridge relative to devices in which only one electric heater is provided or in which a plurality of electric heaters are provided but which are not spaced along the length of the elongate piercing assembly. It may also allow the device to heat parts of a cartridge to which would not be heated by devices having only a single heater, enabling more of the aerosol-forming substrate in each cartridge to be vaporised, reducing waste. Additionally, when used with cartridges having a plurality of different aerosol-forming substrates stored separately, the plurality of longitudinally spaced apart electric heaters allow separate heating of the different aerosol-forming substrates to produce an aerosol with particularly desirable characteristics.

Where the heater assembly comprises a plurality of electric heaters, all of the electric heaters may be fixed to one of the first and second hollow shaft portions. In at least one example embodiment, the plurality of electric heaters comprises one or more electric heaters fixed to the first hollow shaft portion and one or more electric heaters fixed to the second hollow shaft portion. The plurality of electric heaters may be evenly or unevenly divided between the first and second hollow shaft portions. In at least one example embodiment, one of the first and second hollow shaft portions may comprise a single electric heater, with the remaining electric heaters being fixed to the other of the first and second hollow shaft portions.

One or more electric heaters may extend across the airflow passage transverse to the longitudinal axis of the elongate piercing assembly. In at least one example embodiment, the one or more electric heaters may span the airflow passage. In at least one example embodiment, this may place the electric heater directly in the path of being drawn through the device when in use. This may allow vaporised aerosol-forming substrate to be more readily entrained into air flowing through the device to form an aerosol. It may also allow the electric heater to be cooled by the air flowing through the device, reducing the risk of overheating. By extending across the airflow passage, the electric heaters may help to mix the vaporise aerosol-forming substrate with the air flow through the hollow shaft portion, for example by creating turbulence in the air flow. This may result in a more homogenous aerosol when compared to examples in which no electric heaters extend across the airflow passage.

Where the heater assembly comprises a plurality of electric heaters, the plurality of electric heaters ay each extend across the internal airflow passage transverse to the longitudinal direction of the elongate piercing assembly. In at least one example embodiment, the plurality of electric heaters may each span the airflow passage.

Where one or more of the electric heaters extend across the airflow passage, the longitudinal axis of one or more of the electric heaters may be perpendicular to the longitudinal axis of the hollow shaft portion. One or more of the electric heaters extending across the airflow passage may be arranged such that its longitudinal axis is oblique to the longitudinal axis of the hollow shaft portion.

Where the plurality of electric heaters extend across the airflow passage transverse to the longitudinal axis of the hollow shaft portion, one or more of the plurality of electric heaters may extend across the airflow passage such that its longitudinal axis is rotated about the longitudinal axis of the elongate piercing assembly relative to the longitudinal axis of at least one other of the electric heaters. That is, when longitudinal axes of the electric heaters are projected onto a plane extending perpendicularly to the longitudinal axis of the elongate piercing assembly, the longitudinal axis of one or more of the plurality of electric heaters extends across the airflow passage at an angle to the longitudinal axis of at least one other of the electric heaters. With this arrangement, the electric heaters may more readily intercept air flowing through the device relative to arrangements in which the electric heaters are aligned about the longitudinal axis of the elongate piercing assembly. It also means that at least one of the electric heaters may be in fluid communication with the storage portion of a cartridge at a position which is offset around the circumference of the elongate piercing assembly from one or more of the remaining electric heaters. This ray allow the device to more uniformly consume aerosol-forming substrate stored in a cartridge, reducing waste, relative to arrangements in which the electric heaters are aligned about the longitudinal axis of the hollow shaft portion. Additionally, in the event that liquid aerosol-forming substrate leaks from one of the electric heaters during use, by having one or more of the electric heaters extending at a different angle, the liquid may be more readily intercepted and absorbed into one of the adjacent electric heaters and may thus reduce liquid leakage from the device.

In at least one example embodiment, one or both of the first and second hollow shaft portions comprises a plurality of apertures in which the plurality of electric heaters are held, the plurality of electric heaters being in fluid communication with the storage portion of a cartridge received in the cavity through the plurality of apertures.

The apertures may be formed in the first or second hollow shaft portion after the respective hollow shaft portion has been formed, for example by punching, drilling, milling, erosion, electro erosion, cutting, or laser cutting. The apertures may be formed integrally with the first or second hollow shaft portion at the time of forming the hollow shaft portion, for example by casting or moulding the hollow shaft portion with the apertures or by a deposition process, such as electrodeposition.

As used herein, the term "aerosol-generating device" refers to a device that interacts with an aerosol-generating article, such as a consumable cartridge, to generate an aerosol.

In at least one example embodiment, the aerosol-generating device is portable. The aerosol-generating device may have a size comparable to a conventional cigar or cigarette. The aerosol-generating device may have a total length ranging from about 30 mm to about 150 mm. The aerosol-generating device may have an external diameter ranging from about 5 mm to about 30 mm.

The heater assembly may be fixed to, or integral with, the main housing and the closure body of the device. In at least one example embodiment, the heater assembly may be removably fastened to one or both of the main housing and the closure body. This may allow the heater assembly to be at least partially removed from the device, for example for maintenance or cleaning or to enable replacement of the heater assembly. The heater assembly may be removable coupled to the main housing or the closure body by one or more electrical and mechanical connection means.

The heater assembly comprises one or more electric heaters. In at least one example embodiment, the heater assembly may comprise one, two, three, four, five, six or more electric heaters fixed to the elongate piercing assembly. Where the heater assembly comprises one or more electric heaters, the electric heaters may be spaced along the length of the elongate piercing assembly. Each electric heater comprises at least one heating element. Each electric heater may comprise more than one heating element, for example two, or three, or four, or five, or six or more heating elements. The heating element or heating elements may be arranged appropriately so as to most effectively heat the aerosol-forming substrate of a cartridge inserted into the cavity of the main housing.

Each heating element may be a coil of electrically resistive wire. The heating element may be formed by stamping or etching a sheet blank that can be subsequently wrapped around a wick. In at least one example embodiment, the heating element is a coil of electrically resistive wire. The pitch of the coil is ranges from about 0.5 mm to about 1.5 mm. In at least one example embodiment the pitch of the coil is about 1.5 mm. The pitch of the coil means the spacing between adjacent turns of the coil. The coil may comprise fewer than six turns, and may have fewer than five turns. The electrically resistive wire has a diameter ranging from about 0.10 mm to about 0.15 mm. In at least one example embodiment, the electrically resistive wire has a diameter of about 0.125 mm. The electrically resistive wire is formed of 904 or 301 stainless steel. Examples of other suitable metals include titanium, zirconium, tantalum and metals from the platinum group. Examples of other suitable metal alloys include, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America. The heating element may also comprise a metal foil, e.g., an aluminium foil, which is provided in the form of a ribbon.

The at least one heating element may operate by resistive heating. In other words the material and dimensions of the heating element may be chosen so that when a particular current is passed through the heating element the temperature of the heating element is raised to a desired (or, alternatively predetermined) temperature. The current through the heating element may be applied by conduction from a battery or may be induced in the heating element by the application of a variable magnetic field around the heating element.

The at least one heating element may comprise an inductive heating element, such that, where the device forms part of an aerosol-generating system consisting of the aerosol generating device and a removable aerosol-generating article, no electrical contacts are formed between the article and the device. The device may comprise an inductor coil and a power supply configured to provide high frequency oscillating current to the inductor coil. The article may comprise a susceptor element positioned to heat the aerosol-forming substrate. As used herein, a high frequency oscillating current means an oscillating current having a frequency ranging from about 500 kHz to about 10 MHz.

Electric heaters according to at least one example embodiment may comprise a capillary body. The at least one heating element may be arranged on an outer surface of the capillary body, for example as a coil. The capillary body may comprise any suitable material or combination of materials which is able to convey a liquid aerosol-forming substrate along its length. The capillary body may be formed from a porous material, but this need not be the case. The capillary body may be formed from a material having a fibrous or spongy structure. The capillary body comprises a bundle of capillaries. In at least one example embodiment, the capillary body may comprise a plurality of fibres or threads or other fine bore tubes. The capillary body may comprise sponge-like or foam-like material. The structure of the capillary body forms a plurality of small bores or tubes, through which an aerosol-forming liquid can be transported by capillary action. The material or materials will depend on the physical properties of the aerosol-forming substrate. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres, ceramic, glass fibres, silica glass fibres, carbon fibres, metallic fibres of medical grade stainless steel alloys such as austenitic 316 stainless steel and martensitic 440 and 420 stainless steels. The capillary body may have any suitable capillarity so as to be used with different liquid physical properties. The liquid has physical properties, including but not limited to viscosity, surface tension, density, thermal conductivity, boiling point and vapour pressure, which allow the liquid to be transported through the capillary body. The capillary body may be formed from heat-resistant material. In at least one example embodiment, the capillary body may comprise a plurality of fibre strands. The plurality of fibre strands may be generally aligned along the length of the capillary body.

Electric heaters according to at least one example embodiment may comprise a capillary body; a heating element arranged on an outer surface of the capillary body; and a pair of spaced apart electrical contacts fixed around the capillary body and over the heating element for electrically coupling the electric heater to the elongate support member. By fixing the electrical contacts around the capillary body and over the heating element, the electrical contacts may secure the heating element to the outer surface of the capillary body as well as providing an electrical connection. In at least one example embodiment, this may require fewer manufacturing steps than existing systems in which the ends of the heater element are manually connected to the electrical contacts, for example by welding. It may also allow the electric heater to be manufactured on an automated assembly line, so such devices can be manufactured more quickly with high repeatability. In such embodiments, at least one of the electrical contacts is dimensioned such that there is a frictional fit between an inner surface of that electrical contact and the outer surface of the capillary body. Providing such a frictional fit may allow the electrical contact to be secured on the capillary body without the need for additional fastening means or fastening steps. In at least one example embodiment, each electrical contact is dimensioned such that there is a frictional fit between the inner surface of the electrical contact and the outer surface of the capillary body. The heating element may comprise a coil of electrically resistive wire wound around the capillary body, for example along the entire length of the capillary body.

Where electric heaters comprise a capillary body, a heating element arranged on an outer surface of the capillary body, and a pair of spaced apart electrical contacts fixed around the capillary body and over the heating element, the capillary body is compressible and the electrical contacts extend around the circumference of the capillary body such that there is an interference fit between the electrical contacts and the capillary body. This may help to ensure that the heating element is securely fixed to the capillary body by the electrical contact without the need for adhesive or additional fixation steps, such as soldering or welding. It may also help to ensure a reliable electrical connection between the electrical contact and the heating element. The electrical contacts extend around more than about 50 percent of the circumference of the capillary body. This may result in a more secure fixation of the electrical contacts to the capillary body relative to examples in which the electrical contacts extend around less than 50 percent of the circumference of the capillary body. It may also help to ensure a reliable electrical connection between the electrical contact and the heating element.

Where electric heaters comprise a capillary body, a heating element arranged on an outer surface of the capillary body, and a pair of spaced apart electrical contacts fixed around the capillary body and over the heating element, one or both of the electrical contacts may extend around substantially the entire circumference of the capillary body. At least one of the electrical contacts may circumscribe the capillary body. In such example embodiments, the electrical contact may be ring shaped. In at least one example embodiment, both electrical contacts circumscribe the capillary body. This may result in a more secure fixation of the electrical contacts to the capillary body relative to examples in which the electrical contacts extend around less than the entire circumference of the capillary body. It may also help to ensure a reliable electrical connection between the electrical contact and the heating element irrespective of the specific arrangement of the heating element on the outer surface of the capillary body and without restricting the arrangement of the heating element to ensure contact between the electrical contacts and the heating element. In certain embodiments, both electrical contacts circumscribe the capillary body and are dimensioned such that there is an interference fit between the electrical contacts and the capillary body.

Where electric heaters comprise a capillary body, a heating element, and a pair of spaced apart electrical contacts fixed around the capillary body and over the heating element, the electrical contacts may be rigid. This may result in a more robust assembly than one in which the electrical contacts are flexible. The electrical contacts may each comprise a ring of rigid material, such as a metallic ring. This may provide an electrical contact with high mechanical resistance and reliable electrical connection to the heating element. It may also enable the electric heater to be connected to the heater assembly by snap fitting the electrical contacts into a retaining clip in the device. Where the electrical contacts extend around the circumference of the capillary body, the opposed ends of each electrical contact may be co-operatively shaped such that the joint is non-linear or extends along an oblique line. In this context, the term "oblique line" means that the joint extends along a line which is nonparallel to the longitudinal axis of the capillary body. By having a joint which is non-linear or extending along an oblique line, relative movement between the opposed ends of each electrical contact in the longitudinal direction of the capillary body can be substantially prevented and/or reduced.

Where electric heaters comprise a capillary body, a heating element, and a pair of spaced apart electrical contacts fixed around the capillary body and over the heating element, the capillary body may be any suitable shape. In certain embodiments, the capillary body is elongate. The pair of electrical contacts may be spaced apart in a length direction of the capillary body. For example, the pair of electrical contacts may comprise a first electrical contact at or adjacent to a first end of the capillary body and a second electrical contact at any other location, such as at a midpoint along the length of the capillary body. The pair of electrical contacts may comprise a first electrical contact at or adjacent to a first end of the capillary body and a second electrical contact at or adjacent to the second end of the capillary body.

Where electric heaters comprise a capillary body, the electric heater may further comprise a rigid support member extending along at least part of the length of the capillary body. The rigid support member increases the strength and rigidity of the electric heater to ensure a robust assembly which is easy to handling during manufacture. The rigid support member may be formed from a single, unitary component or from a plurality of components connected together. The rigid support member may extend through the core of the capillary body. The support member may be surrounded by the capillary body. The support member may be circumscribed by the capillary body. The presence of the rigid support member may reduce the overall radial compressibility of the capillary body, thus helping to ensure a tight fit between the electrical contacts and the heating element. The support member may be arranged on an outer surface of the capillary body. In some examples, the rigid support member comprises a central portion and a plurality of transverse ribs. This cross-sectional shape may result in a support member having a suitable rigidity without occupying a large amount of space within the capillary body and thus significantly reducing the wicking ability of the capillary body. The plurality of transverse ribs may comprise a plurality of radially extending ribs.

In at least one example embodiment, one or both of the first and second hollow shaft portions may be electrically conductive. The electrically conductive hollow shaft portion or portions may comprise a plurality of apertures, wherein the one or more electric heaters may be formed by one or more narrow regions of the hollow shaft portion between adjacent apertures.

In at least one example embodiment, having a heater assembly with one or more integral electric heaters may require fewer manufacturing steps and may allow the heater assembly to be manufactured on an automated assembly line. This may allow aerosol-generating devices to be manufactured more quickly, simply and with high repeatability and consistency. Such devices may be simplified, less expensive and more robust than devices in which the heater assembly comprises complicated and potentially fragile connections.

The apertures may be formed in one or both hollow shaft portions after the hollow shaft portion has been formed, for example by punching, drilling, milling, erosion, electro erosion, cutting, or laser cutting. The apertures may be formed integrally with the hollow shaft portion at the time of forming the hollow shaft portion, for example by casting or moulding the hollow shaft portion with the apertures or by forming the hollow shaft portion with the apertures in a deposition process, such as electrodeposition.

As used herein, "electrically conductive" means formed from a material having a resistivity of $1\times10^{-4}$ $\Omega$m, or less. As used herein, "electrically insulating" means formed from a material having a resistivity of $1\times10^{4}$ $\Omega$m or more.

The at least one electric heater may be arranged on the hollow shaft portion in any suitable manner. In some example embodiments, the at least one electric heater circumscribes the hollow shaft portion. This may allow for more even heating of the aerosol-forming substrate in the cartridge relative to devices in which the at least one electric heater does not circumscribe the hollow shaft portion. The at least one electric heater may circumscribe the hollow shaft portion continuously. The at least one electric heater may circumscribe the hollow shaft portion discontinuously in the form of a plurality of electric heaters spaced apart in the circumferential direction of the hollow shaft portion. In other example embodiments, the at least one electric heater may extend around only part of the circumference of the hollow shaft portion.

Devices according to at least one example embodiment comprise a main housing and a closure body. The main housing may be elongate. The main housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. In at least one example embodiment, the material is Light and non-brittle.

In at least one example embodiment, devices may further comprise electric circuitry connected to the heater assembly and to an electrical power source. The electric circuitry may comprise a microprocessor, which may be a programmable microprocessor, a microcontroller, or an application specific integrated chip (ASIC) or other electronic circuitry capable of providing control. The electric circuitry may comprise further electronic components. The electric circuitry may be configured to regulate a supply of current to the heater assembly. Current may be supplied to the heater assembly continuously following activation of the device or may be supplied intermittently, such as on a puff by puff basis. The electric circuitry may comprise DC/AC inverter, which may comprise a Class-D or Class-E power amplifier.

The device comprises a power supply within the housing. In at least one example embodiment, the power supply may be a battery such as a lithium iron phosphate battery, or another form of charge storage device such as a capacitor. The power supply may require recharging and may have a capacity that allows for the storage of enough energy for one or more smoking experiences. In at least one example embodiment, the power supply may have sufficient capacity to allow for the continuous generation of aerosol for a period of around six minutes, corresponding to the typical time taken to smoke a cigarette, or for a period that is a multiple of six minutes. In at least one example embodiment, the power supply may have sufficient capacity to allow for a desired (or, alternatively predetermined) number of puffs or discrete activations.

The device may comprises power supply connected to the heater assembly and electric circuitry connected to the power supply and to the heater assembly.

Where the heater assembly comprises a plurality of electric heaters which are fixed to and spaced along the length of the elongate piercing assembly, the electric circuitry is configured to measure one or more electrical parameters of the plurality of electric heaters and to calculate an estimated remaining amount of aerosol forming substrate in the cartridge or an estimated distribution of aerosol forming substrate in the cartridge, based on the measured electrical parameters.

As used herein, the term "electrical parameter" is used to describe an electrical property, value or attribute that can be quantified by measurement, for example, resistivity, conductivity, impedance, capacitance, current, voltage, and resistance.

In at least one example embodiment, with this arrangement, the electric heaters have dual functionality: heating and sensing. This may allow the device to determine at any time an estimate of the state of the aerosol-forming substrate remaining in the cartridge. From this, the device may be operated differently by the electric circuitry to maintain desirable aerosol properties, or may indicate the current state of the aerosol-forming substrate to allow an adult vaper to take appropriate action, such as changing the cartridge or the orientation of the device.

In such example embodiments, the electric circuitry is configured to separately measure the one or more electrical parameters of each of the plurality of electric heaters and to calculate the estimated remaining amount, or the estimated distribution, or the estimated remaining amount and the estimated distribution, based on differences in the measured electric parameters of two or more of the plurality of electric heaters.

Where the device comprises a power supply connected to the heater assembly and electric circuitry connected to the power supply and to the heater assembly, the device further comprises an indicator connected to power supply. The electric circuitry may be configured to operate the indicator in response to the estimated remaining amount or the estimated distribution. The indicator may have any suitable configuration, for example the indicator may be for example a display, an audio output, a haptic output, or any combination thereof. This may allow the device to convey information regarding the estimated remaining amount or the estimated distribution, or both, of liquid aerosol-for substrate in the cartridge.

The electric circuitry may be configured to operate the indicator when the estimated remaining amount falls below a threshold value to alert the adult vaper and to prompt the adult vaper into replacing the cartridge. The control circuitry may be configured to operate the indicator when the estimated distribution suggests that device has been held at a particular angle for too long so that the device may be reoriented, at least temporarily, so that the aerosol-forming substrate may be redistributed in the storage portion.

The control circuitry may be configured to inform an adult vaper about the estimated remaining amount or estimated distribution via a communication link with a separate device, such as a smartphone, swart-watch, tablet, desktop computer, or similar device.

Where the device comprises electric circuitry connected to a power source and configured to measure one or more electrical parameters of the plurality of electric heaters and to calculate an estimated remaining amount or estimated distribution, the electric circuitry may be further configured to control a supply of power to one or more of the plurality of electric heaters separately in response to the estimated remaining amount or the estimated distribution.

In at least one example embodiment, this may allow the device to determine which of the electric heaters is in the best condition to generate aerosol in the most effective way and to vary the supply of power accordingly. This may help to substantially minimise and/or reduce variations in aerosol properties caused by variations in the distribution of the aerosol-forming substrate within the cartridge. It may also reduce overall energy consumption of the device by allowing the energy draw of the electric heaters to be selected in the most effective manner. The electric circuitry may be configured to increase the supply of power to one or more of the plurality of electric heaters in response to the estimated remaining amount or the estimated distribution.

The electric circuitry may be configured to reduce the supply of power to one or more of the plurality of electric heaters in response to the estimated remaining amount or the estimated distribution.

In at least one example embodiment, this may allow the energy consumption of one or more of the electric heaters to be selectively reduced, for example where the estimated remaining amount or estimated distribution indicates that a particular electric heater is not well placed to generate an aerosol. It may also reduce the risk of damage to the electric heaters due to over heating, for example where a liquid aerosol-forming substrate is used and the electrical parameters indicate that one or more of the electric heaters is dry or partially dry.

The electric circuitry may be configured to reduce or increase the supply of power to one or more of the plurality of electric heaters in response to the estimated remaining amount or the estimated distribution. The electric circuitry may be configured to reduce the supply of power to one or more of the plurality of electric heaters while simultaneously increasing the supply of power to a different one or more of the plurality of electric heaters, in response to the estimated remaining amount or the estimated distribution.

At least one example embodiment relates to an electrically heated aerosol-generating system comprising an electrically heated aerosol-generating device according to any of the example embodiments described above, and a consumable cartridge comprising a storage portion containing an aerosol forming substrate. The storage portion has a fluid permeable internal surface surrounding an open-ended passage extending through the cartridge. The cartridge is enclosed in the cavity such that the elongate piercing assembly extends into the open-ended passage of the cartridge.

The system comprises a consumable cartridge. The consumable cartridge may be removably coupled to the aerosol-generating device. As used herein, the term 'removably coupled' is used to mean that the cartridge and device can be coupled and uncoupled from one another without significantly damaging either the device or cartridge. The cartridge may be removed from the aerosol-generating device when the aerosol-forming substrate has been consumed. The cartridge may be disposable. The cartridge may be reusable. The cartridge may be refillable with aerosol-forming substrate. The cartridge may be replaceable in the aerosol-generating device.

The aerosol-generating system may comprise an aerosol-forming chamber in which aerosol forms from a super saturated vapour and is then carried through the air outlet. An air inlet, the air outlet and the chamber are arranged so as to define an airflow route from the air inlet to the air outlet via the aerosol-forming chamber, so as to convey the aerosol to the air outlet. The aerosol-forming chamber may be defined by one or both of the cartridge and the aerosol-generating device.

As used herein, the term 'aerosol-forming substrate' relates to a substrate capable of releasing volatile compounds that can form an aerosol. Such volatile compounds may be released by heating the aerosol-forming substrate. An aerosol-forming substrate may be part of an aerosol-generating article, such as a cartridge, or smoking article.

The aerosol-forming substrate is an aerosol-forming liquid. As used herein, the terms "aerosol-forming liquid" and "liquid aerosol-forming substrate" are interchangeable. The storage portion comprises a capillary wick forming part or all of the internal surface for transporting liquid aerosol-forming substrate from the storage portion to the heater assembly.

The storage portion may contain a single aerosol-forming substrate. The storage portion may contain two or more aerosol-for substrates stored separately. In at least one example embodiment, the storage portion may contain three aerosol-forming substrates stored separately, four aerosol-forming substrates stored separately, five aerosol-forming substrates stored separately, or six or more aerosol-forming substrates stored separately. Where the storage portion contains two or more aerosol-forming substrates stored separately, the heater assembly comprises a plurality of electric heaters spaced along the length of the elongate piercing assembly, the plurality of electric heaters including at least one electric heater for each of the aerosol-forming substrates, each of the electric heaters being configured to heat its corresponding aerosol-forming substrate. This allows the aerosol-forming substrates to be heated independently.

In at least one example embodiment, the storage portion of the consumable cartridge contains first and second aerosol forming substrates stored separately and the heater assembly comprises a plurality of electric heaters spaced along the length of the elongate piercing assembly. The plurality of electric heaters comprises a first electric heater configured to heat the first aerosol forming substrate to form a first aerosol and a second electric heater configured to heat the second aerosol forming substrate to form a second aerosol.

In at least one example embodiment, the storage portion is compressible and the diameter of the open-ended passage extending through the cartridge is less than the outer diameter of one or both of the first and second hollow shaft portions. With this arrangement, the storage portion may be radially compressed by the piercing assembly to ensure a tight fit between the cartridge and the respective hollow shaft portion. This may facilitate contact between the electric heaters and the aerosol-forming substrate in the storage portion to allow consistent aerosol properties. It may also restrict or eliminate air flow between the cartridge and the outside of the hollow shaft portion, thereby facilitating the delivery of a consistent aerosol.

At least one example embodiment relates to a consumable cartridge for an electrically heated aerosol-generating device according to any of the example embodiments described above. The cartridge comprises a storage portion containing an aerosol-forming substrate, a fluid permeable internal surface surrounding an open ended passage extending through the cartridge, a first frangible seal across a first end of the open-ended passage, and a second frangible seal across a second end of the open-ended passage.

The open-ended passage within the cartridge may allow for a system that is compact. It may also allow the cartridge to be used in a system which is symmetrical and balanced which is may be helpful when the system is a handheld system. An internal passage may also substantially minimise and/or reduce heat losses from the device and allow the housing of the device and cartridge to be easily maintained at a temperature than is comfortable to hold.

The open-ended passage forms a guiding and aligning means that co-operates with the elongate piercing assembly of devices to facilitate the correct orientation and position of the cartridge into the device.

As used herein, the term "fluid permeable surface" refers to a surface that allows liquid or gas to permeate through it. The internal surface may have a plurality of openings formed in it to allow fluid to permeate through it.

The upstream and downstream ends of the cartridge may be capped by frangible seals. The cartridge may further include a sealing ring at one or both of the upstream and downstream ends of the open-ended passageway.

In at least one example embodiment, the aerosol forming substrate comprises a liquid aerosol forming substrate.

The storage portion contains first and second aerosol forming substrates stored separately. The first and second aerosol-forming substrates may be different.

The cartridge may comprise a first sealed compartment comprising a first aerosol-forming substrate and a second sealed compartment comprising a second aerosol-forming substrate. The first compartment and the second compartment are arranged in series from the upstream end to the downstream end of the cartridge. That is, the second compartment is downstream of the first compartment. In at least one example embodiment, each of the first compartment and the second compartment comprises a frangible barrier at each end. The frangible barrier is configured such that the barrier can be pierced by the elongate support member when the cartridge is inserted into the aerosol-generating device. In at least one example embodiment, each frangible barrier is made from metal film, such as an aluminium film. In at least one example embodiment, the first compartment and the second compartment of the cartridge abut one another. In at least one example embodiment, the first compartment and the second compartment may be spaced apart. The volume of the first compartment and the second compartment may be the same or different. In at least one example embodiment, the volume of the second compartment is greater than the volume of the first compartment.

The storage portion forms an annular space surrounding the internal open-ended passage. The cartridge may have a generally cylindrical shape and may have any desired cross-section, such as circular, hexagonal, octagonal or decagonal.

In at least one example embodiment, the storage portion may comprise a tubular porous element in which a liquid aerosol-forming substrate is absorbed.

The storage portion comprises a capillary wick and a capillary material containing liquid aerosol-forming substrate. The capillary wick may define the internal surface surrounding the open-ended passage. A capillary material is a material that actively conveys liquid from one end of the material to another. The capillary material may be oriented in the storage portion to convey liquid aerosol-forming substrate to the open-ended passage. The capillary material may have a fibrous structure. The capillary material may have a spongy structure. The capillary material may comprise a bundle of capillaries. The capillary material may comprise a plurality of fibres. The capillary material may comprise a plurality of threads. The capillary material may comprise fine bore tubes. The capillary material may comprise a combination of fibres, threads and fine-bore tubes. The fibres, threads and fine-bore tubes may be generally aligned to convey liquid to the electric heater. The capillary material may comprise sponge-like material. The capillary material may comprise foam-like material. The structure of the capillary material may form a plurality of small bores or tubes, through which the liquid can be transported by capillary action.

The capillary material may comprise any suitable material or combination of materials. Examples of suitable materials are a sponge or foam material, ceramic- or graphite-based materials in the form of fibres or sintered powders, foamed metal or plastics materials, a fibrous material, for example made of spun or extruded fibres, such as cellulose acetate, polyester, or bonded polyolefin, polyethylene, terylene or polypropylene fibres, nylon fibres or ceramic. The capillary material may be made of a polymeric compound, including medical grade polymers such as ALTUGLAS® Medical Resins Polymethlymethacrylate (PMMA), Chevron Phillips K-Resin® Styrene-butadiene copolymer (SBC), Arkema special performance polymers Pebax®, Rilsan®, and Rilsan® Clear, DOW (Health+™) Low-Density Polyethylene (LDPE), DOW™ LDPE 91003, DOW™ LDPE 91020 (MFI 2.0; density 923), ExxonMobil™ Polypropylene (PP)

PP1013H1, PP1014H1 and PP9074MED, Trinseo CALIBRE™ Polycarbonate (PC) 2060-SERIES. The capillary material may be made of a metallic alloy, for example aluminium or stainless steel medical grade alloys. The capillary material may have any suitable capillarity and porosity so as to be used with different liquid physical properties. The liquid aerosol-forming substrate has physical properties, including but not limited to viscosity, surface tension, density, thermal conductivity, boiling point and atom pressure, which allow the liquid to be transported through the capillary material by capillary action. The capillary material may be configured to convey the aerosol-forming substrate to the atomiser.

In at least one example embodiment, the aerosol-forming substrate may be an aerosol-forming liquid. In such example embodiments, the storage portion is a liquid storage portion for storing the aerosol-forming liquid.

The liquid aerosol-forming substrate may comprise nicotine. The nicotine containing liquid aerosol-forming substrate may be a nicotine salt matrix. The liquid aerosol-forming substrate may comprise plant-based material. The liquid aerosol-forming substrate may comprise tobacco. The liquid aerosol-forming substrate may comprise a tobacco-containing material containing volatile tobacco flavour compounds, which are released from the aerosol-forming substrate upon heating. The liquid aerosol-forming substrate may comprise homogenised tobacco material. The liquid aerosol-forming substrate may comprise a non-tobacco-containing material. The liquid aerosol-forming substrate may comprise homogenised plant-based material.

The liquid aerosol-forming substrate may comprise at least one aerosol-former. An aerosol-former is any suitable known compound or mixture of compounds that facilitates formation of a dense and stable aerosol and that is substantially resistant to thermal degradation at the temperature of operation of the system. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Aerosol formers may be polyhydric alcohols or mixtures thereof, such as triethylene glycol, 3-butanediol and glycerine. The liquid aerosol-forming substrate may comprise other additives and ingredients, such as flavourants.

The aerosol-forming substrate may comprise nicotine and at least one aerosol former. The aerosol former may be glycerine. The aerosol-former may be propylene glycol. The aerosol former may comprise both glycerine and propylene glycol. The aerosol-forming substrate may have a nicotine concentration ranging from about 2% to about 10% by weight based on the weight of the aerosol-forming substrate.

Although reference is made to liquid aerosol-forming substrates above, other forms of aerosol-forming substrate may be used with other example embodiments. In at least one example embodiment, the aerosol-forming substrate may be a solid aerosol-forming substrate. The aerosol-forming substrate may comprise both solid and liquid components. The aerosol-forming substrate may comprise a tobacco-containing material containing volatile tobacco flavour compounds which are released from the substrate upon heating. The aerosol-forming substrate may comprise a non-tobacco material. The aerosol-for substrate may further comprise an aerosol former. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco, cast leaf tobacco and expanded tobacco. The solid aerosol-forming substrate may be in loose form, or may be provided in a suitable container or cartridge. In at least one example embodiment, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

As used herein, homogenised tobacco refers to material formed by agglomerating particulate tobacco. Homogenised tobacco may be in the form of a sheet. Homogenised tobacco material may have an aerosol-former content of greater than about 5% on a dry weight basis. Homogenised tobacco material may alternatively have an aerosol former content ranging from about 5% to about 30% by weight on a dry weight basis. Sheets of homogenised tobacco material may be formed by agglomerating particulate tobacco obtained by grinding or otherwise comminuting one or both of tobacco leaf lamina and tobacco leaf stems. Alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof.

In at least one example embodiment, the solid aerosol-forming substrate may be provided on or embedded in a thermally stable carrier. The carrier may take the form of powder, granules, pellets, shreds, spaghettis, strips or sheets. In at least one example embodiment, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

Also provided is a kit for an electrically heated aerosol-generating system, the kit comprising an electrically heated aerosol generating device according to any of the embodiments described above, and a plurality of consumable cartridges according to any of the embodiments described above.

As used herein, the terms 'upstream' and 'downstream' are used to describe the relative positions of components, or portions of components, of cartridges, aerosol-generating devices and aerosol-generating systems in relation to the direction of air drawn through the cartridges, aerosol-generating devices and aerosol-generating systems during use thereof. The terms 'distal' and 'proximal', are used to describe the relative positions of components of aerosol-generating devices and aerosol-generating systems in relation to their connection to the device, such that the proximal end of a component is at the 'fixed' end which is connected to the device, and the distal end is at the 'free' end, opposite to the proximal end. Where a component is connected to the device at the downstream end of the component, the downstream end may be considered as the 'proximal' end, and vice versa.

As used herein, the terms "longitudinal" and "length" refer to the direction between the opposed ends of the cartridge, the device, or a component of the device, such as between its downstream or proximal end and the opposed upstream or distal end. The term "transverse" is used to describe the direction perpendicular to the longitudinal direction.

The upstream and downstream ends of the cartridge and the aerosol-generating device are defined with respect to the airflow when a draw on the mouth end of the aerosol-generating device occurs. Air is drawn into the cartridge or the device at its upstream end, passes downstream through the cartridge or the device and exits the cartridge or device at its downstream end.

As used herein, the term "air inlet" is used to describe one or more apertures through which air may be drawn into the aerosol-generating system.

As used herein, the term "air outlet" is used to describe one or more aperture through which air may be drawn out of the aerosol-generating system.

Features described in relation to one or more example embodiments may equally be applied to other example embodiment. In particular, features described in relation to the aerosol-generating device of the one example embodiment may be equally applied to the aerosol-generating system of other example embodiments, and vice versa.

FIG. 1 is a schematic illustration of an aerosol-generating system 10 according to at least one example embodiment comprising an aerosol-generating device 100 and an aerosol-generating article in the form of a consumable cartridge 200.

The device 100 comprises a main housing 102 containing a battery 104 and control electronics 106. The main housing 102 also defines a cavity 108 into which the cartridge 200 is received. The device 100 further includes a closure body in the form of a mouthpiece portion 110 including an outlet 112. In this example embodiment, the mouthpiece portion 110 is connected to the main housing 102 by a screw fitting, but any suitable kind of connection may be used, such as a hinged connection or a snap fitting. The device 100 further includes a heater assembly 300 comprising an elongate piercing assembly 302 and a plurality of electric heaters 400 supported by the piercing assembly 302. The elongate piercing assembly 302 is positioned centrally within the cavity 108 of the device 100 and extends along the longitudinal axis of the cavity 108. The piercing assembly 302 comprises a first hollow shaft portion 304 connected to the main housing 102 and a second hollow shaft portion 324 connected to the mouthpiece portion 110 via mouthpiece connectors 311. The first and second hollow shaft portions 304, 324 extend along the same longitudinal axis and meet at a junction 330 such that the elongate piercing assembly extends along the entire length of the cavity 108. The first and second hollow shaft portions 304, 324 together define an internal airflow passage 306 extending along the elongate piercing assembly 302. Air inlets 114 are provided in the main housing 102 upstream of the heater assembly 300 and are in fluid communication with the outlet 112 via the airflow passage 306.

Figure 2:
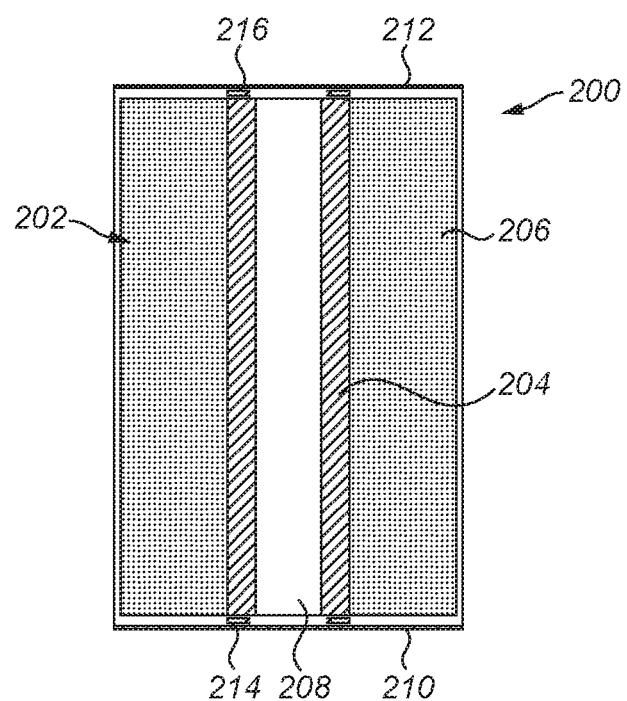
FIG. 2 illustrates a longitudinal cross-section of a consumable cartridge for use with the aerosol-generating system of FIG. 1 according to at least one example embodiment.

As best seen in FIG. 2, the cartridge 200 comprises a storage portion 202 including a tubular capillary wick 204 surrounded by a tubular capillary material 206 containing liquid aerosol-forming substrate. The cartridge 200 has a hollow cylindrical shape through which extends an internal passageway 208. The capillary wick 204 surrounds the internal passageway 208 so that the internal passageway 208 is at least partly defined by an inner surface of the capillary wick 204. The upstream and downstream ends of the cartridge 200 are capped by frangible seals 210, 212. The cartridge 200 further includes a sealing ring 214, 216 at each of the upstream and downstream ends of the internal passageway 208.

Figure 3A:
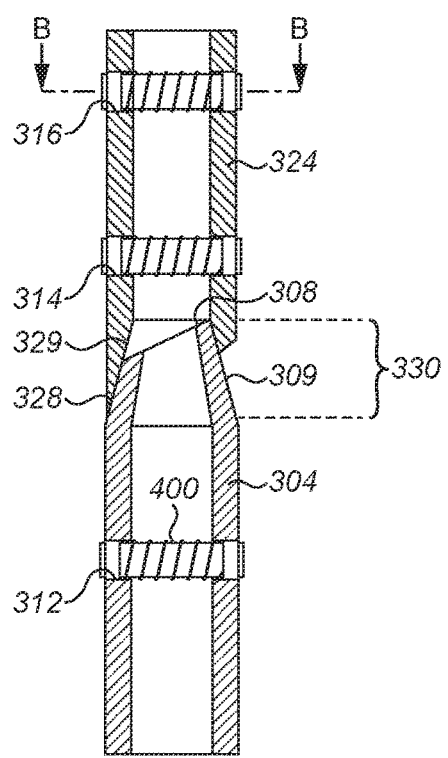
FIG. 3A illustrates a longitudinal cross-section of a heater assembly for the aerosol-generating system of FIG. 1 according to at least one example embodiment.
Figure 3B:
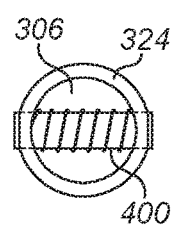
FIG. 3B illustrates a distal end view of the heater assembly of FIG. 3A according to at least one example embodiment.
Figure 3C:
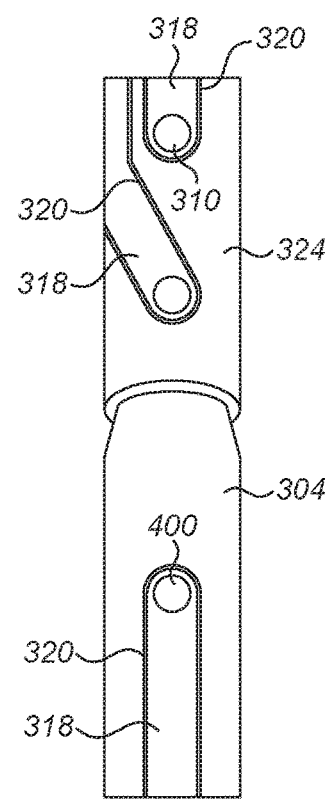
FIG. 3C illustrates a side view of the heater assembly of FIG. 3A according to at least one example embodiment.

As shown in FIGS. 3A, 3B and 3C, the first hollow shaft portion 304 has a piercing surface 308 at its distal, or downstream end and the second hollow shaft portion 324 has a piercing surface 328 at its distal, or upstream end. In this example embodiment, the piercing surfaces 308 are each formed by a sharp tip at the distal end of the first and second hollow shaft portions 304, 324. The distal end of the first hollow shaft portion 304 has an inwardly tapering outer surface 309 and the distal end of the second hollow shaft portion 324 has an outwardly tapering inner surface 329, the outer and inner surfaces 309 and 329 being co-operatively shaped such that the outer surface 309 of the first hollow shaft portion 304 fits within the inner surface 329 of the second hollow shaft portion 324 to form a seal around the junction 330.

In at least one example embodiment, the heater assembly 300 includes three electric heaters 400 fixed to and spaced along the length of the elongate piercing assembly. One of the electric heaters 400 is fixed to the first hollow shaft portion 304 while the remaining two electric heaters 400 are fixed to the second hollow shaft portion 324. It will be appreciated the heater assembly may comprise any suitable number of electric heaters. In at least one example embodiment, the heater assembly may comprise a single electric heater, or two, three, four, five, six, seven, or eight or more electric heaters fixed to and spaced apart along the length of the elongate piercing member. Where the heater assembly comprises a plurality of electric heaters, these may be divided equally or unequally between the first and second hollow shaft portions.

Each of the electric heaters 400 is held within a plurality of apertures 310 in the first and second hollow shaft portions 305, 324. The apertures 310 are provided in pairs, with each pair supporting a single electric heater 400 at both of its ends. The two apertures in each pair are spaced apart around the circumferences of the hollow shaft portions 304, 324 so that each of the electric heaters 400 extends across the airflow passage 306. In at least one example embodiment, the plurality of apertures 310 comprises three pairs of apertures 312, 314, 316 supporting three electric heaters 400. The three pairs of apertures 312, 314, 316 are spaced apart along the length of the elongate piercing assembly 302 and aligned around the circumferences of the hollow shaft portions 304, 324 such that the longitudinal axes of the three electric heaters 400 are parallel and rotationally aligned. It will be appreciated that other arrangements of heater assembly are envisaged. In at least one example embodiment, three alternative arrangements of heater assembly are discussed below in relation to FIGS. 6A to 6C, FIGS. 7A and 7B and FIG. 8.

The first and second hollow shaft portions 304, 324 are both electrically conductive and at least partially divided into a plurality of electrically isolated sections 318, each associated with one or more electric heaters 400 and each electrically connected to the battery in the device. In the case of the first hollow shaft portion 304, the electrically isolated sections 318 are connected to the battery by electrical connections (not shown) at the base of the first hollow shaft portion 304. In the case of the second hollow shaft portion 324, electrically isolated sections 318 may be electrically connected to the battery in the device via the first hollow shaft portion 304 and the junction 330, or via the mouthpiece connectors between the second hollow shaft portion 324 and the mouthpiece portion 110 and via electrical connections (not shown) between the mouthpiece portion 110 and the main housing 102.

The apertures 310 are each formed in one of the electrically isolated sections 318. The electrically isolated sections 318 are electrically isolated from each other by insulating gaps 320. Thus, the electric heaters 400 may be electrically isolated from the each other to allow separate operation, control, or monitoring, without the need for separate electrical wiring for each heater. In this example, the gaps 320 are air gaps. That is, the gaps 320 do not contain insulating material. In other examples, one or more of the gaps 320 may be filled or partially filled with an electrically insulating material.

Figure 4A:
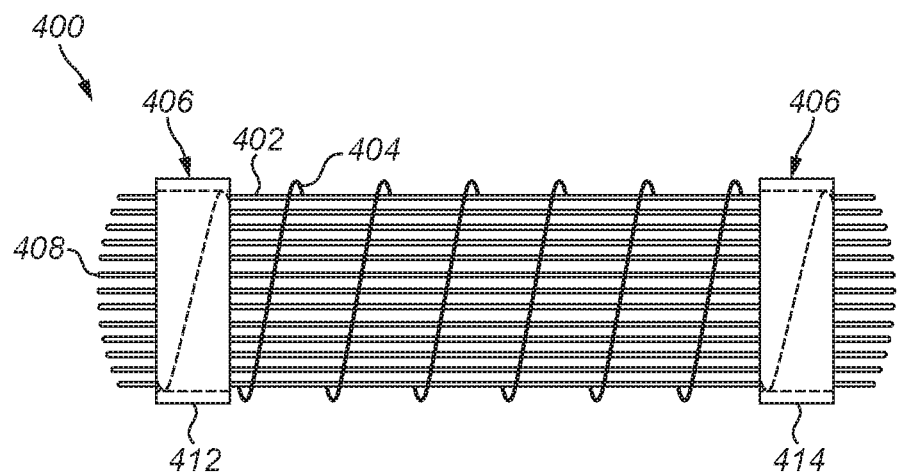
FIG. 4A illustrates a side view of an electric heater for the heater assembly of the aerosol-generating system of FIG. 1 according to at least one example embodiment.
Figure 4B:
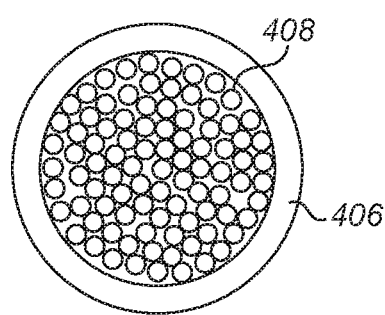
FIG. 4B illustrates an end view of the electric heater of FIG. 4A according to at least one example embodiment.
Figure 4C:
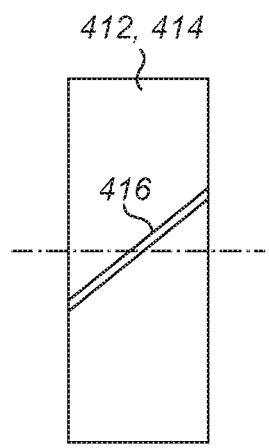
FIG. 4C illustrates a side view of an electric contact of the electric heater of FIG. 4A, with the other components of the electric heater removed for clarity according to at least one example embodiment.

As best seen in FIGS. 4A to 4C, each electric heater 400 comprises a capillary body 402, a heating element 404 arranged on an outer surface of the capillary body 402, and a pair of spaced apart electrical contacts 406 fixed around the capillary body 402 and over the heating element 404. The capillary body 402, or capillary wick, comprises a plurality of fibres 408 through which an aerosol-forming liquid can be transported by capillary action. In this example, the plurality of fibres 408 are generally aligned along the length of the capillary body 402. In other example embodiments, the plurality of fibres may be woven or braided in a specific pattern. This allows the physical characteristics of the capillary wick, such as mechanical strength or capillarity, to be altered by using a particular pattern of fibres. It may also allow the capillary wick to maintain its shape and dimensions more effectively than with parallel fibres. The capillary body is compressible, for example due to the presence of interstices between adjacent fibres. In this example embodiment, the ends of the capillary body 402 are rounded or domed. This may help to increase the surface area between the capillary body 402 and an aerosol-forming liquid in the cartridge 200. In other example embodiments, the ends of the capillary body 402 may be flat or planar.

The heating element 404 of each electric heater 400 is formed from a coil of electrically resistive wire wound around the capillary body 402 and extending along its entire length. The wire may have any suitable cross-sectional shape. In at least one example embodiment, the wire has a round cross-sectional shape. In at least one example embodiment, the wire may have an oval, triangular, square, rectangular, or flat cross-sectional shape. This may increase heat transfer between the fibres 408 of the capillary body 402 and the heating element 404.

The electrical contacts 406 of each electric heater 400 comprise a first metallic ring 412 at a first end of the capillary body 402 and a second metallic ring 414 at a second end of the capillary body 402. The first and second rings 412, 414 extend around the entire circumference of the capillary body 402 and over the heating element 404. The inner diameter of each of the rings 412, 414 is less than the outer diameter of the capillary body 402. Consequently, there is an interference fit between the rings 412, 414 and the capillary body 402 underneath. This ensures that the rings 412, 414 press into the capillary body 402 and are secured thereto, with the heating element 404 retained between. This helps to ensure a reliable electrical connection between the electrical contacts 406 and the heating element 404. As the electrical contacts 406 extend around the entire circumference of the capillary body 402, it is not necessary to carefully match the rotational position of the electrical contacts with the position of the heating coil 404 during assembly to ensure an electrical connection.

The first and second rings 412, 414 of the electrical contacts 406 are rigid and formed from a bent sheet of metal. The opposed ends of the bent sheet are connected together at a joint 416. In this example, the opposed ends are co-operatively shaped such that the joint 416 extends along an oblique line. This helps each of the electrical contacts 406 to maintain its shape by resisting relative movement between its opposed ends in the length direction of the electric heater 400. In at least one example embodiment, the opposed ends may be co-operatively shaped so that joint has a non-linear shape, such as a wavy, sinusoidal, parabolic, U-, V-, curved, or zig-zag shape. Again, this helps each of the electrical contacts 406 to maintain its shape for the reasons discussed above.

In the example embodiment shown in FIGS. 4A to 4C, the capillary body 402 has a circular cross-section and the electrical contacts 406 are in the form of circular rings. However, in other example embodiments, the capillary body 402 and electrical contacts 406 may have any suitable cross-sectional shape. In at least one example embodiment, the capillary body and electrical contacts may have an oval, triangular, square, rectangular, or lozenge-shaped cross-sectional shape.

The electrical contacts 406 and the apertures 310 in the elongate piercing assembly 302 are co-operatively sized to provide a frictional fit. This ensures a secure fit between the hollow shaft portion 304 and the electric heaters 400. This may also enable a good electrical connection to be maintained between the heating element of each electric heater and the battery 104 in the device 100. In at least one example embodiment, the apertures 310 are circular to match the shape of the electrical contacts of the electric heaters 400. In other examples, the cross-sectional shape of the electrical contacts may be different and the shape of the apertures determined accordingly. In at least one example embodiment, the electrical contacts may have one or more outwardly extending tabs and the first and second hollow shaft portions may have corresponding notches around the apertures which form ports into which the tabs may be received. Alternatively, or in addition, the elongate piercing assembly 302 may include one or more clips in which the tabs may be located and retained.

Figure 5A:
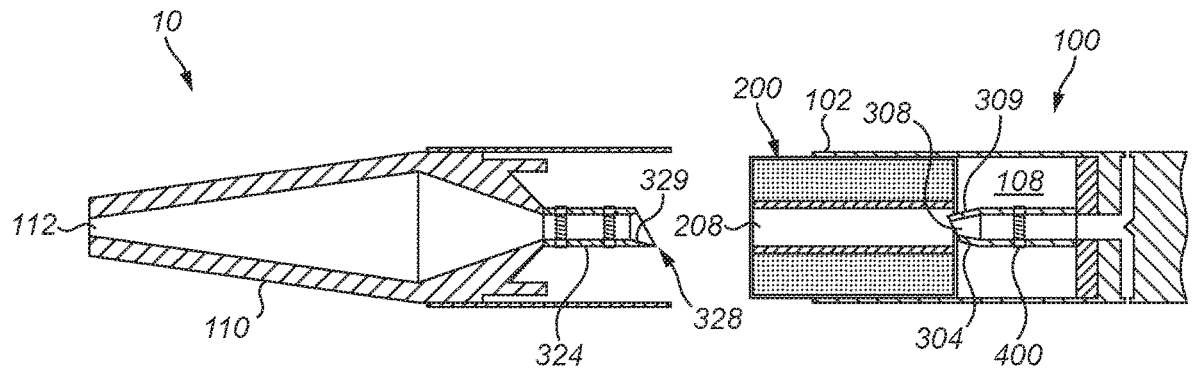
FIGS. 5A to 5C illustrate a method of inserting a consumable cartridge into the aerosol-generating device of the aerosol-generating system of FIG. 1 according to at least one example embodiment.
Figure 5B:
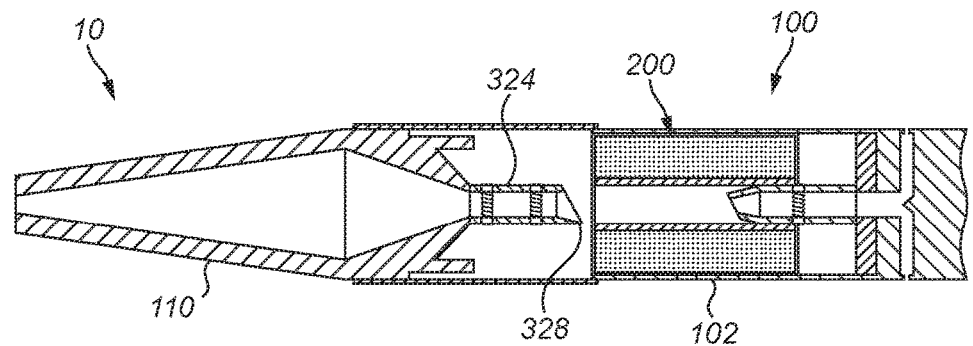
Figure 5C:
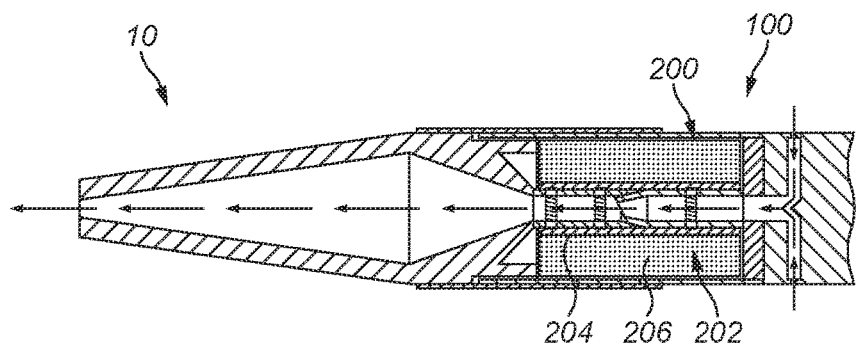

Referring to FIGS. 5A, 5B and 5C, insertion of the cartridge 200 into the device 100 of the system 10 will now be described.

To insert the cartridge 200 into the device 100, and thereby assemble the system 10, the first step is to remove the mouthpiece portion 110 from the main housing 102 of the device 100 and to insert the article 200 into the cavity 108 of the device 100. During insertion of cartridge 200 into the cavity 108, the first piercing surface 308 at the distal end of the first hollow shaft portion 304 breaks the first frangible seal at the upstream end of the cartridge 200, as shown in FIG. 5A.

The mouthpiece portion 110 is then placed over the end of the main housing 102 so that the second hollow shaft portion 324 is aligned with the internal passageway in the cartridge 200, as shown in FIG. 5B.

As the mouthpiece portion 110 is further engaged with the main housing 102, the second piercing surface 328 at the distal end of the second hollow shaft portion 324 engages with and breaks through the second frangible seal at the downstream end of the cartridge 200 to create a hole in the second frangible seal. The mouthpiece portion 110 is then fully engaged with the main housing 102 to fully insert and enclose the cartridge 200 in the cavity 108, as shown in FIG. 5C.

When the cartridge 200 is fully inserted into the cavity 108, the holes in the first and second frangible seals at the upstream and downstream ends of the cartridge 200 caused by the first and second hollow shaft portions 304, 324 each have a diameter approximately equal to the outer diameters of the hollow shaft portions 304, 324. The sealing rings at the upstream and downstream ends of the cartridge 200 form a seal around the hollow shaft portions 304, 324. Together with the frangible seals this reduces or prevents leakage of liquid aerosol-forming substrate from the cartridge 200 and out of the system 10.

As also shown in FIG. 5C, when the cartridge 200 is fully inserted into the cavity 108 of the aerosol-generating device 100, an airflow pathway, shown by arrows in FIG. 5C, is formed through the aerosol-generating system 10 via the internal passageway 208 in the cartridge 200 and the airflow passage 306 in the heater assembly 1300. As further shown in FIG. 5C, when the cartridge 200 is fully inserted, the electric heaters 400 are in fluid communication with the storage portion 202 of the cartridge 200 via the capillary wick 204 at the inner surface of the internal passageway 208 of the cartridge 200 and via the apertures in the first and second hollow shaft portions 304, 324.

In at least one example embodiment, during vaping, liquid aerosol-forming substrate is transferred from the storage portion 202 to the capillary body 402 of each electric heater 400 via capillary action and through the plurality of apertures in the first and second hollow shaft portions 304, 324. In at least one example embodiment, the outer diameter of the first and second hollow shaft portions 304, 324 of the elongate piercing assembly 302 is greater than the inner diameter of the internal passageway 208 of the cartridge 200 so that the storage portion 202 of the cartridge 200 is compressed by the heater assembly 300. This ensures direct contact between the ends of the electric heaters 400 and the storage portion 202 to help transfer of liquid aerosol-forming substrate to the electric heaters 400.

The battery supplies electrical energy to the heating element of each electric heater 400, via the first and second hollow shaft portions 304, 324 and the electrical contacts 406. The heating elements heat up to vaporise liquid substrate in the capillary body of the electric heaters 400 to create a supersaturated vapour. At the same time, the liquid being vaporised is replaced by further liquid moving along the capillary wick of the liquid storage portion 202 and the capillary body of each electric heater 400 by capillary action. (This is sometimes referred to as "pumping action".) When draw is taken on the mouthpiece portion 110, air is drawn through the air inlets 114, through the airflow passage of the hollow shaft portion 304, past the electric heaters 400, into the mouthpiece portion 110 and out of the outlet 112. The vaporised aerosol-forming substrate is entrained in the air flowing through the airflow passage of the hollow shaft portion 304 and condenses within the mouthpiece portion 110 to form an inhalable aerosol, which is carried towards the outlet 112.

The device may be operated by a manually operated switch (not shown) on the device 100. Alternatively, or in addition, the device may include a sensor for detecting a puff or draw. When a puff is detected by the sensor, the control electrics control the supply of electrical energy from the battery to the electric heaters 400. The sensor may comprise one or more separate components. In some example embodiments, the puff sensing function is performed by the heating elements of the heater and wick assemblies. In at least one example embodiment, by measuring with the control electronics one or more electrical parameters of the heating elements and detecting a particular change in the measured electrical parameters which is indicative of a puff.

During operation of the system, the distribution of liquid aerosol-forming substrate in the cartridge may change. In at least one example embodiment, as the liquid aerosol-forming substrate in the storage portion is depleted, or where the system is held at an angle for a sufficient period of time. This change in the distribution of liquid aerosol-forming substrate may lead to differences in the amount of liquid in the capillary body of each electric heater and, consequently, the temperature of the heating element of each electric heater. This is discussed below in relation to FIG. 6.

Figure 5D:
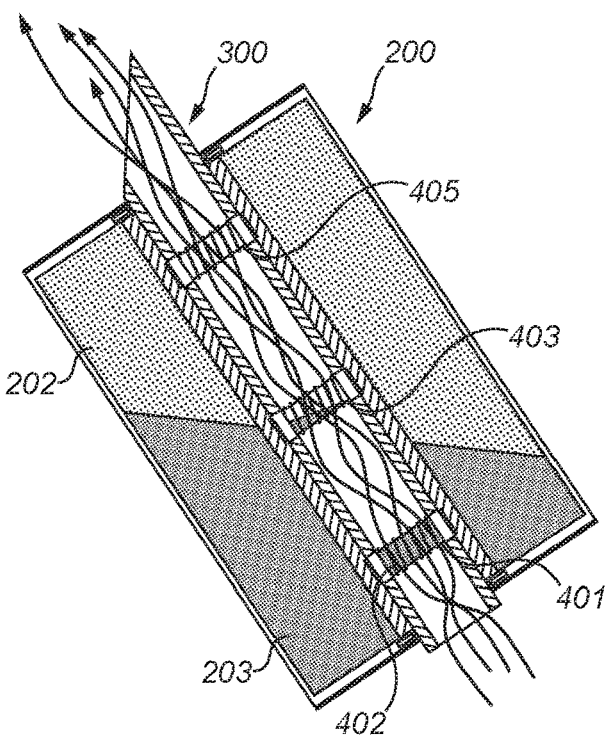
FIG. 5D illustrates a longitudinal cross-section of the cartridge and heater assembly of the system of FIGS. 5A to 5C in which the system is held in a tilted position according to at least one example embodiment.

FIG. 5D shows a longitudinal cross-section of the cartridge 200 and heater assembly 300 of the aerosol-generating system following a period in which the system has been held in a tilted position. As shown, the remaining liquid 203 in the cartridge 200 has settled in the storage portion 202 at an angle to the heater assembly 300. As the electric heaters are spaced apart along the length of the cartridge 200, the amount of liquid aerosol-forming substrate drawn up by the capillary bodies of the electric heaters is not uniform. In at least one example embodiment, the capillary body 402 of the first electric heater 401 at the upstream end of the heater assembly 300 is saturated with liquid aerosol-forming substrate, while the second electric heater 403 midway along the length of the heater assembly 300 is only partially wet with liquid aerosol-forming substrate, and the third electric heater 405 at the downstream end of the heater assembly 300 is dry. In at least one example embodiment, the electric heaters 401, 403, 405 run at different temperatures. As the electrical parameters of each electric heater, such as the resistivity, conductivity, impedance, capacitance, current, voltage, and resistance of the heating element, may vary as a function of the temperature, the distribution of the liquid aerosol-forming substrate or the remaining amount of liquid aerosol-forming substrate may be estimated by the control circuitry through measuring the electrical parameters of each electric heater. The control electronics is configured to separately measure one or more electrical parameters of each electric heater during use and to calculate an estimated remaining amount, or estimated distribution, of liquid aerosol-forming substrate in the cartridge based on differences in the measured electrical parameters from the electric heaters. Thus, the electric heaters function both as heaters and as sensors.

The device includes an indicator (not shown), such as a display or audio or haptic output, connected to the control circuitry, which may be used to convey information regarding the estimated remaining amount of liquid aerosol-forming substrate in the cartridge 200. When the estimated remaining amount falls below a threshold level, the electric circuitry may also be configured to operate the indicator to alert the adult vaper and to indicate that the cartridge needs changing. The control circuitry may also be configured to estimated the distribution of liquid aerosol-forming substrate in the cartridge based on differences in the measured electrical parameters from the electric heaters and to operate the indicator when the estimated distribution suggests that system has been held at a particular angle for too long to alert that the orientation of the device 100 should be altered, at least temporarily, to allow the liquid aerosol-forming substrate to be redistributed in the storage portion. In this, or other example embodiments, the control circuitry may be configured to alert an adult vaper about the estimated remaining amount or estimated distribution via a communication link with a separate device, such as a smartphone, swart-watch, tablet, desktop computer, or similar device.

In addition to detecting differences in electrical parameters in the electric heaters 400 and calculated an estimated remaining amount, or estimated distribution, of liquid aerosol-forming substrate in the cartridge 200, the control circuitry 106 is also configured to control the supply of electrical power to each of the electric heaters 400 in response to the estimated remaining amount, or estimated distribution. In at least one example embodiment, where the measured electrical parameters indicate that one or more of the electric heaters 400 is partially dry, the control electronics 106 is configured to reduce the supply of electrical energy to that electric heater. This allows the system 10 to determine which of the electric heaters 400 is in the best condition to generate aerosol in the most effective way. This allows adverse changes to the properties of aerosol generated by the system 10, caused by variations in wetness and temperature across the electric heaters, to be substantially minimised and/or reduced. It may also reduce energy consumption of the system 10, and reduce the risk of damage to the electric heaters due to over heating. Where the electrical parameters indicate that one or more of the electric heaters 400 is dry, the control electronics 106 is configured to reduce the supply of electrical energy to that electric heater to zero.

Figure 6A:
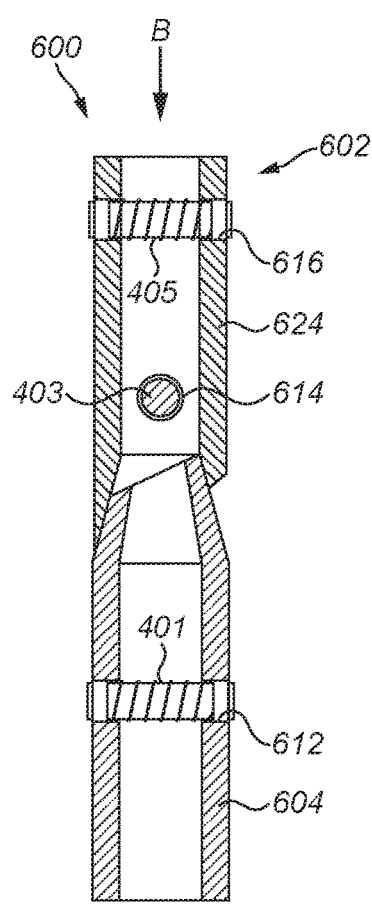
FIG. 6A illustrates a longitudinal cross-section of a second embodiment of heater assembly for the aerosol-generating system of FIG. 1 according to at least one example embodiment.
Figure 6B:
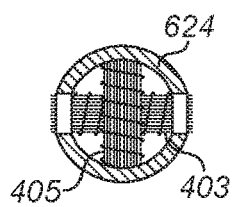
FIG. 6B illustrates a distal end view of the heater assembly of FIG. 6A, in the direction of arrow B in FIG. 6A according to at least one example embodiment.
Figure 6C:
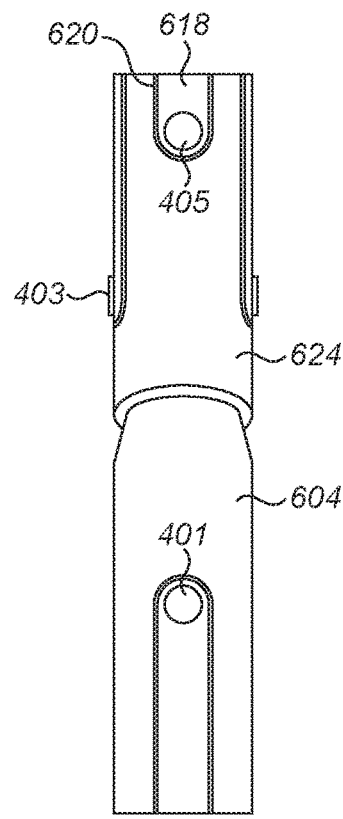
FIG. 6C illustrates a side view of the heater assembly of FIG. 6A according to at least one example embodiment.

FIGS. 6A, 6B and 6C illustrate a heater assembly 600 according to at least one example embodiment. The heater assembly 600 has a similar structure to the heater assembly 300 of example embodiments described above and where the same features are present, like reference numerals have been used. As with the heater assembly of the first embodiment, the elongate piercing member 602 formed by the first and second hollow shaft portions 604, 624 comprises three pairs of apertures 612, 614, 616 in which three electric heaters 401, 403, 405 are held such that their longitudinal axes are parallel in the transverse direction. However, unlike in the heater assembly 300 of the first embodiment, in the heater assembly 600 according to a second embodiment, the central, second pair of apertures 614 is offset around the circumference of the first hollow shaft portion 604 by 90 degrees relative to the first and third pairs of apertures 612, 616. Consequently, the longitudinal axis of the central electric heater 403 is rotated by 90 degrees about the longitudinal axis of the hollow shaft portions 604, 624 relative to the first and second electric heaters 401, 405. This may allow for more efficient use of the liquid aerosol-forming substrate in the cartridge in comparison to the heater assembly 300 of the first embodiment.

Figure 7A:
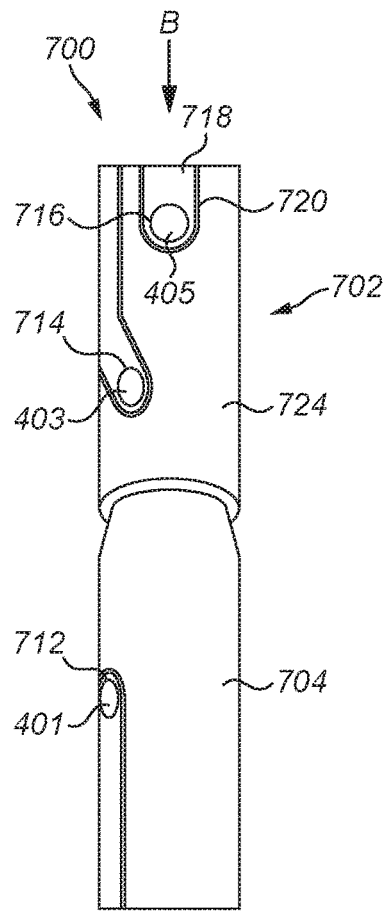
FIG. 7A illustrates a longitudinal cross-section of a heater assembly for the aerosol-generating system of FIG. 1 according to at least one example embodiment.
Figure 7B:
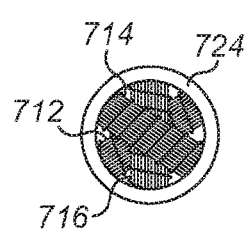
FIG. 7B illustrates a distal end view of the heater assembly of FIG. 7A according to at least one example embodiment.

FIGS. 7A and 7B illustrate a heater assembly 700 according to at least one example embodiment. The heater assembly 700 has a similar structure to the example embodiments of heater assembly 300 and 600 and where the same features are present, like reference numerals have been used. As with the heater assembly 600, the hollow shaft portion 704 comprises three pairs of apertures 712, 714, 716 in which three electric heaters 401, 403, 405 are held such that their longitudinal axes are parallel in the transverse directions. However, unlike in the heater assembly 600, in the heater assembly 700, the pairs of apertures 712, 714, 716 are each offset around the circumference of the first and second hollow shaft portions 704, 724 so that the longitudinal axes of the electric heaters 401, 403, 405 are parallel in the transverse direction but rotated about the longitudinal axis of the hollow shaft portions 704, 724 relative to each other. The longitudinal axis of each electric heater 401, 403, 405 is rotated by a uniform amount of less than about 90 degrees from its adjacent electric heater or heaters. Consequently, the electric heaters 401, 403, 405 are arranged in a spiral, or helix, pattern along the elongate piercing member 702. In at least one example embodiment, the electric heaters may be rotated about the longitudinal axis of the hollow shaft portions 704, 724 by a non-uniform amount.

Figure 8:
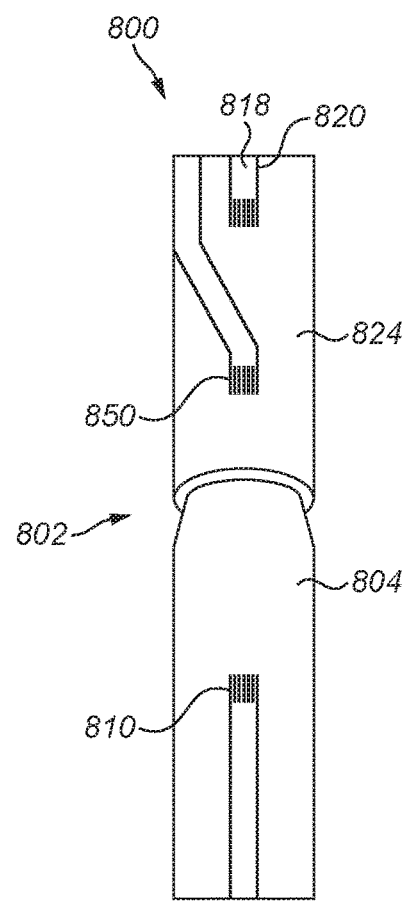
FIG. 8 illustrates a side view of a fourth embodiment of heater assembly for the aerosol-generating system of FIG. 1 according to at least one example embodiment.

FIG. 8 illustrates a heater assembly 800 according to at least one example embodiment. As with the heater assemblies 300, 600 and 700 of other example embodiments described herein, the heater assembly 800 comprises an elongate piercing assembly 802 comprising first and second electrically conductive hollow shaft portions 804, 824 defining an airflow passage. Again, the first and second hollow shaft portions 804, 824 comprise a plurality of apertures 810 spaced apart along the length of the elongate piercing assembly 802 and are at least partially divided into a plurality of electrically isolated sections 818 which are separated from each other by insulating gaps 820. The apertures 810 of the heater assembly 800 are not arranged to support separate electric heaters. Instead, the apertures 810 are arranged in a plurality of groups of apertures 810 spaced apart along the length of the elongate piercing assembly 802, with each group of apertures 810 defining an electric heater 850 comprising one or more heating elements formed by narrow regions of the hollow shaft portion 804, 824 located between adjacent apertures 810. In this manner, the electric heaters 850 are defined by the hollow shaft portions 804, 824 themselves. The groups of apertures 810, and thus the electric heaters 850, are each formed such that they extend between two of the electrically isolated sections 818. In the example shown in FIG. 8, the electric heaters 850 are each located at the end of a different electrically isolated section 818. In this manner, the electric heaters 850 are electrically isolated from each other by the insulating gaps 820. The apertures 810 are sized so that, when in use, liquid aerosol-forming substrate is drawn in to the electric heaters 850 by capillary action through the apertures 810. In at least one example embodiment, as shown in FIG. 8, the groups of apertures 810 are aligned around the circumference of the hollow shaft portions 804, 824. In other example embodiments, two or more of the groups of apertures 810 may be offset around the circumferences of the hollow shaft portions 804, 824.

The example embodiments described above illustrate but do not limit the invention. It is to be understood that other example embodiments may be made and the example embodiments described herein are not exhaustive.

We claim:

1. An electrically heated aerosol-generating device for use with a consumable cartridge comprising a storage portion containing an aerosol-forming substrate, the storage portion having a fluid permeable internal surface surrounding an open ended passage extending through the cartridge, the device comprising:
 a main housing having a cavity for receiving a cartridge;
 a closure body engageable with the main housing to enclose the cartridge in the cavity; and a heater assembly for heating the cartridge, the heater assembly including,
an elongate piercing assembly configured to extend into the open ended passage of the cartridge and defining an internal airflow passage forming part of an airflow pathway through the device, the elongate piercing assembly including,
a first hollow shaft portion connected to the main housing, the first hollow shaft portion having a first piercing surface at a distal end thereof, the first piercing surface configured to break through a first frangible seal across a first end of the open ended passage when the cartridge is inserted into the cavity, and
a second hollow shaft portion connected to the closure body, the second hollow shaft portion having a second piercing surface at a distal end thereof, the second piercing surface configured to break through a second frangible seal across a second end of the open ended passage when the closure body is engaged with the main housing, the first and second hollow shaft portions extending along a same longitudinal axis when the closure body is engaged with the main housing, and the first and second hollow shaft portions being sized to meet at a junction such that the elongate piercing assembly extends along an entire length of the cavity when the closure body is engaged with the main housing; and
at least one electric heater fixed to the elongate piercing assembly, the at least one electric heater having at least one heating element for heating the aerosol forming substrate when the cartridge is enclosed in the cavity.

2. The electrically heated aerosol-generating device according to claim 1, wherein the distal end of the first hollow shaft portion and the distal end of the second hollow shaft portion are each co-operatively shaped such that a seal is formed around the junction.

3. The electrically heated aerosol-generating device according to claim 2, wherein the distal end of one of the first hollow shaft portion and the second hollow shaft portion has an inwardly tapering outer surface and the distal end of the other one of the first and second hollow shaft portions has an outwardly tapering inner surface, the inner and outer surfaces being shaped such that the inwardly tapering outer surface fits within the outwardly tapering inner surface to form the seal when the closure body is engaged with the main housing.

4. The electrically heated aerosol-generating device according to claim 1, wherein the closure body forms a mouthpiece portion through which air can be drawn through the airflow pathway of the aerosol generating device.

5. The electrically heated aerosol-generating device according to claim wherein the first hollow shaft portion and the second hollow shaft portion are electrically conductive and arranged to connect the one or more electric heaters to an electrical power supply.

6. The electrically heated aerosol-generating device according to claim 1, wherein the heater assembly comprises:
a plurality of electric heaters, the plurality of heaters being fixed to and spaced along a length of the elongate piercing assembly.

7. The electrically heated aerosol-generating device according to claim 6, wherein the plurality of electric heaters comprises:
one or more electric heaters fixed to the first hollow shaft portion; and
one or more electric heaters fixed to the second hollow shaft portion.

8. The electrically heated aerosol-generating device according to claim 6, wherein each of the plurality of electric heaters extend across the internal airflow passage transverse to a longitudinal direction of the elongate piercing assembly.

9. The electrically heated aerosol-generating device according to claim 6, wherein at least one of the first hollow shaft portion and the second hollow shaft portion comprises:
a plurality of apertures in which the plurality of electric heaters are held, the plurality of electric heaters being in fluid communication with the storage portion of a cartridge received in the cavity through the plurality of apertures.

10. An electrically heated aerosol-generating system comprising:
an electrically heated aerosol-generating device according to claim 1; and
a consumable cartridge including,
a storage portion configured to contain an aerosol forming substrate, the storage portion having a fluid permeable internal surface surrounding an open ended passage extending through the cartridge, the cartridge being enclosed in the cavity such that the elongate piercing assembly extends into the open ended passage of the cartridge.

* * * * *